(12) United States Patent
Harel et al.

(10) Patent No.: US 7,620,148 B2
(45) Date of Patent: Nov. 17, 2009

(54) X-RAY DIFFRACTION (XRD) MEANS FOR IDENTIFYING THE CONTENT IN A VOLUME OF INTEREST AND A METHOD THEREOF

(75) Inventors: Ze'ev Harel, Ganot Hader (IL); Asaf Zuk, Jerusalem (IL); Zeev Burshtein, Be'er-Sheva (IL)

(73) Assignee: Xurity Ltd., Ganoy Hadar (IL)

( * ) Notice: Subject to any disclaimer, the term of this patent is extended or adjusted under 35 U.S.C. 154(b) by 199 days.

(21) Appl. No.: 10/597,142

(22) PCT Filed: Jan. 11, 2005

(86) PCT No.: PCT/IL2005/000037

§ 371 (c)(1),
(2), (4) Date: Jul. 12, 2006

(87) PCT Pub. No.: WO2005/065039

PCT Pub. Date: Jul. 21, 2005

(65) Prior Publication Data

US 2007/0111881 A1    May 17, 2007

(30) Foreign Application Priority Data

Jan. 12, 2004   (IL)   ..................................... 159824

(51) Int. Cl.
*G01N 23/20*   (2006.01)
*G01N 23/207*  (2006.01)
*G01T 1/36*    (2006.01)

(52) U.S. Cl. .............................. 378/70; 378/75; 378/83

(58) Field of Classification Search ..................... 378/4, 378/6, 7, 9, 19, 70, 86–90, 57, 75, 83
See application file for complete search history.

(56) References Cited

U.S. PATENT DOCUMENTS

| | | | | |
|---|---|---|---|---|
| 4,821,303 A | * | 4/1989 | Fawcett et al. | ................. 378/80 |
| 5,600,303 A | * | 2/1997 | Husseiny et al. | ......... 340/568.1 |
| 6,118,849 A | * | 9/2000 | Tanimori et al. | ............... 378/71 |
| 2001/0033636 A1 | | 10/2001 | Hartick | |
| 2003/0169843 A1 | | 9/2003 | Ries et al. | |
| 2006/0067471 A1 | * | 3/2006 | Hopkins et al. | ............ 378/98.8 |

* cited by examiner

*Primary Examiner*—Irakli Kiknadze
(74) *Attorney, Agent, or Firm*—Martin Fleit; Paul D. Bianco; Fleit Gibbons Gutman Bongini & Bianco PL

(57) ABSTRACT

The present invention discloses an XRD means for identifying the content of a volume of interest (VOI) and a method thereof. A remote XRD means is comprised inter alia of a plurality of x-ray sources target toward the VOI. A plurality of x-ray detectors adapted to receive diffracted X-rays. A processor adapted to measure the diffracted x-ray patterns. A database comprising records of patterns parameters; and, an alerting means adapted for identifying material as one of the predetermined groups in the record. This invention also discloses a method of acquiring XRD image of a material in a VOI, comprised of receiving VOI coordinates; irradiating the material in the VOI; acquiring, extracting and converting of XRD patterns of the VOI to standard powder X-ray diffraction spectrum; matching records in a database for material identification; and alerting when the material is in a matching predetermined record.

5 Claims, 10 Drawing Sheets

Figure 1:
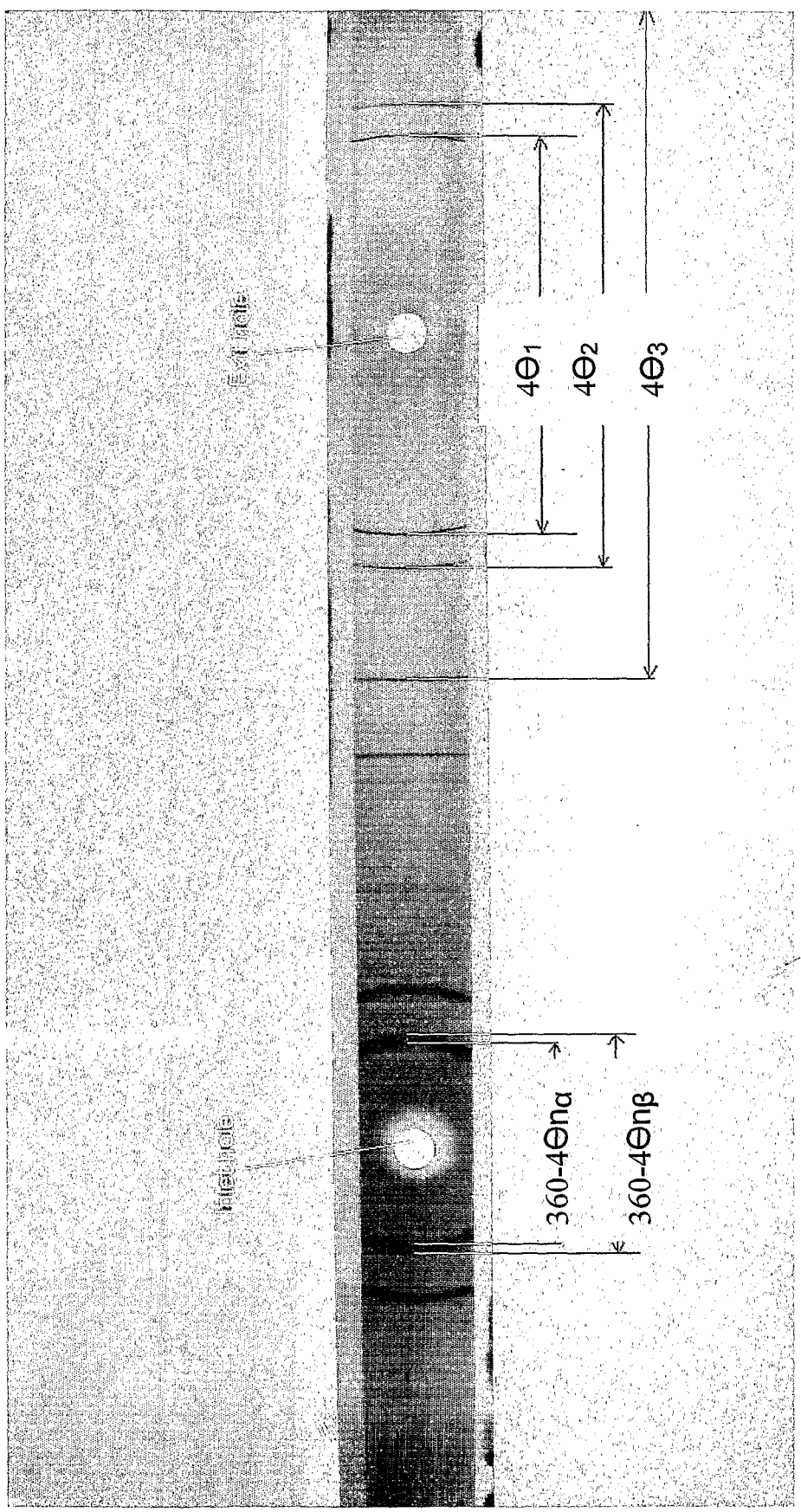

X-RAY DIFFRACTION (XRD) MEANS FOR IDENTIFYING THE CONTENT IN A VOLUME OF INTEREST AND A METHOD THEREOF

FIELD OF THE INVENTION

The present invention generally relates to an XRD means for identifying the content in a volume of interest and to a method thereof.

BACKGROUND OF THE INVENTION

Crystalline materials can be identified by their x-ray diffraction (XRD) pattern, which is unique to each material and can serve as its 'fingerprint'. Among materials that present security hazards are explosives, illegal drugs and spores (e.g. Anthrax spores). The patent suggests a remote detection method to identify suspect materials according to their XRD pattern. The suspect material in a Volume of Interest (VOI), may be recognized by lower stage detection systems, such as: X-ray imaging system, Average density identification by multiple energy X-ray system, NMR (MRI), NQR, IR imaging, millimeter wave imaging, THz imaging, etc.

If monochromatic X-rays impinge upon a polycrystalline sample with randomly oriented crystallites, then some of the crystallites fulfill Bragg's law with respect to the x-ray beam. Thus, all reflections belonging to a particular lattice plane are distributed upon the mantle of a circular cone, of which the x-ray beam is the axis and the aperture angle is 4θ. An x-ray sensitive film or an X-ray detector placed perpendicularly to the x-ray beam will thus record a diffraction image comprising a series of a series of concentric circles. The Bragg angle is given by equation (1):

$$\theta = \frac{1}{2} \arctan \frac{D}{2x} \quad (1)$$

where D is the diameter of a diffraction ring, and x is the distance between the sample and the film.

A variety of X-ray detectors have been presented in the art. Digital Radiography X-ray recording comprises the steps of capturing X-ray photons and converting the recorded signal to an electrical signal. These systems are intrinsically pixelated to form either a pixelated array or a continuous array with a moving "pixelated-bridge" ("pixelated-bridge" means a one-dimensional or very narrow two-dimensional scanning pixel array). The detectors may be divided into two main groups, namely direct and indirect detectors. Direct detectors use a plurality of photo-conducting materials such as silicon, germanium, selenium, CdTe, CdZnTe, $PbI_2$ or $HgI_2$, and are adapted for directly converting x-ray energy into electric charge utilizing TFT (Thin Film Transistor), CMOS (Complementary Metal-Oxide Semiconductor) technology or any other type of substrate whether continuous or pixelated array. This charge can be then captured, stored and recorded. Indirect detectors use a plurality of scintillator materials such as NaI, CsI or $Gd_2O_2S$, to convert the x-ray energy into visible or UV light, which must be optically coupled to a photosensitive device, e.g. a photo-diode array or charge coupled device (CCD). This photo sensor then converts the light into electric charge, which can be captured, stored and recorded. Indirect conversion is a two-step process wherein X-rays are first converted by a means of a scintillator or phosphor material to lower energy, e.g. visible light, photons that are then collected and converted into an electric charge. Commercially available products of GE Medical Equipment Inc. comprising an amorphous silicon flat panel with a Cesium Iodide scintillator is an example of such a technique.

Direct conversion is a single conversion step process. At least three types are known in the art: TFT, CMOS and Continuous plates. The TFT is coated with a photoconductor, wherein the detector uses direct conversion of x-ray energy into electrical signals. No light-emitting materials, intermediate steps and/or additional processes are required to capture and convert the incident x-ray energy. The commercially available products of Hologic Inc. are an example of this type, wherein an amorphous selenium photoconductor is used. Continuous plates are scanned by means of a moving pixelated-bridge. A selenium-based sensor is used to convert incident X-rays into an electric charge image. The charge image is transformed into a digital image using this bridge, which eliminates the need for costly and often-problematic active matrix arrays. The commercially available products of Edge Medical Devices Ltd. and its Scanned Matrix Array Readout Technology (SMART) uses this technology.

US Pat. Application 2001/0033636 to Hartick et al. (now abandoned) discloses a method and apparatus for determining a material of a detected item and deals with a specific method of defining a VOI by means of calculating the average density of the detected volume and a correlation between the VOI and the XRD shots.

U.S. Pat. No. 6,839,406 to Ries et al. presents a method and an apparatus for detecting unacceptable items in objects, such as in luggage, wherein a detector apparatus, functioning as a second detector stage is divided into a lower level testing stage and a higher level testing stage. This invention deals with a novel and yet specific energy dispersion method of XRD.

BRIEF DESCRIPTION OF THE INVENTION

Figure 2:
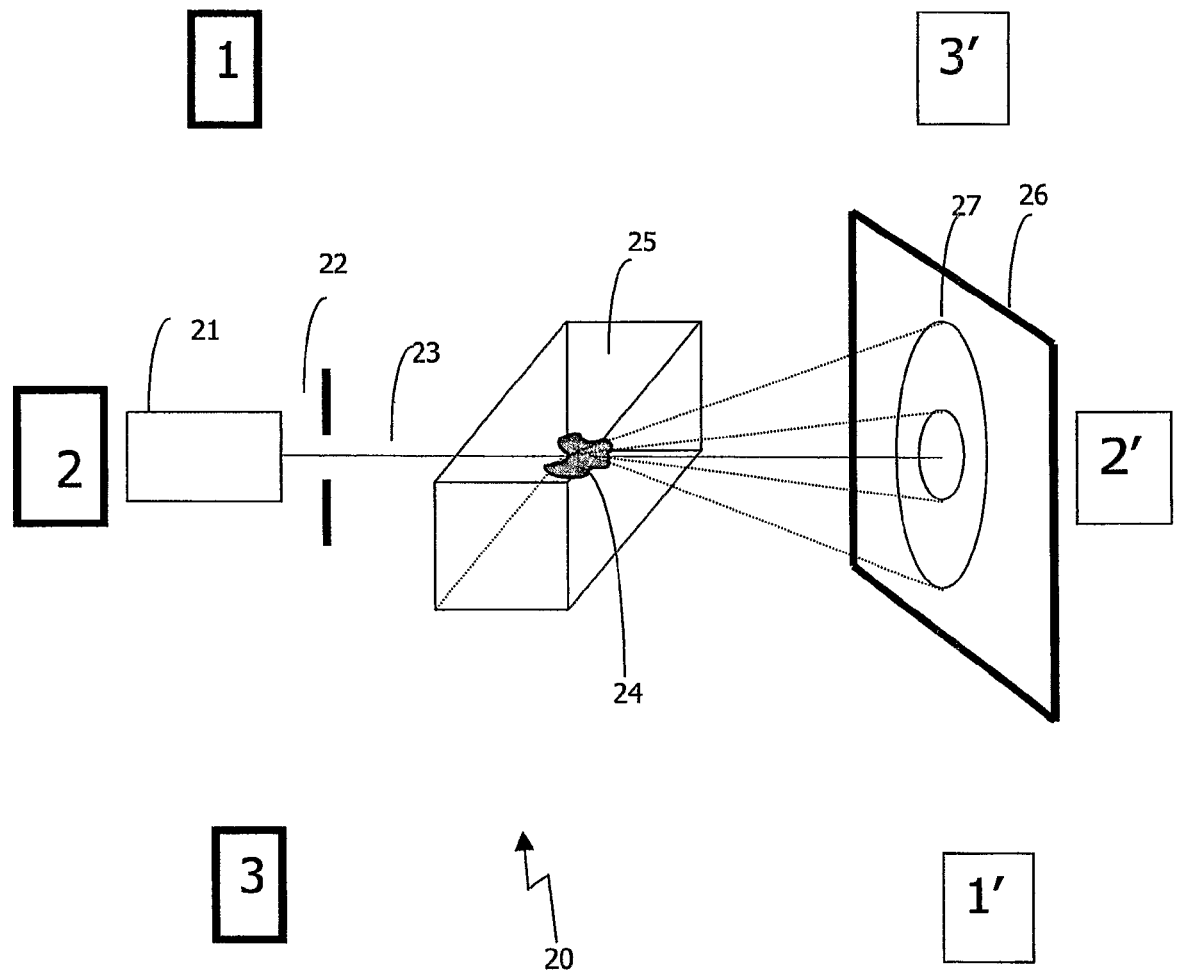
Figure 3:
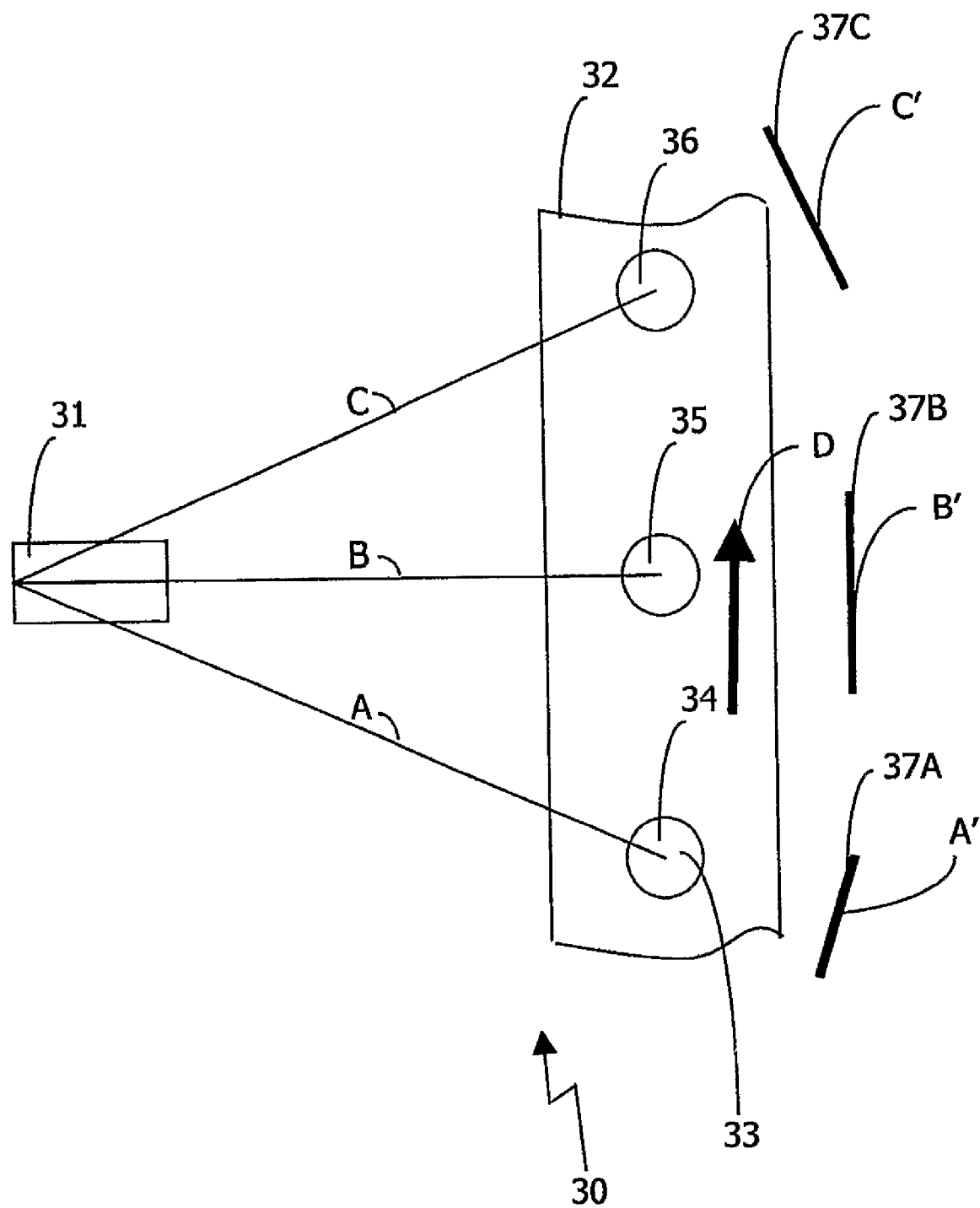
Figure 4:
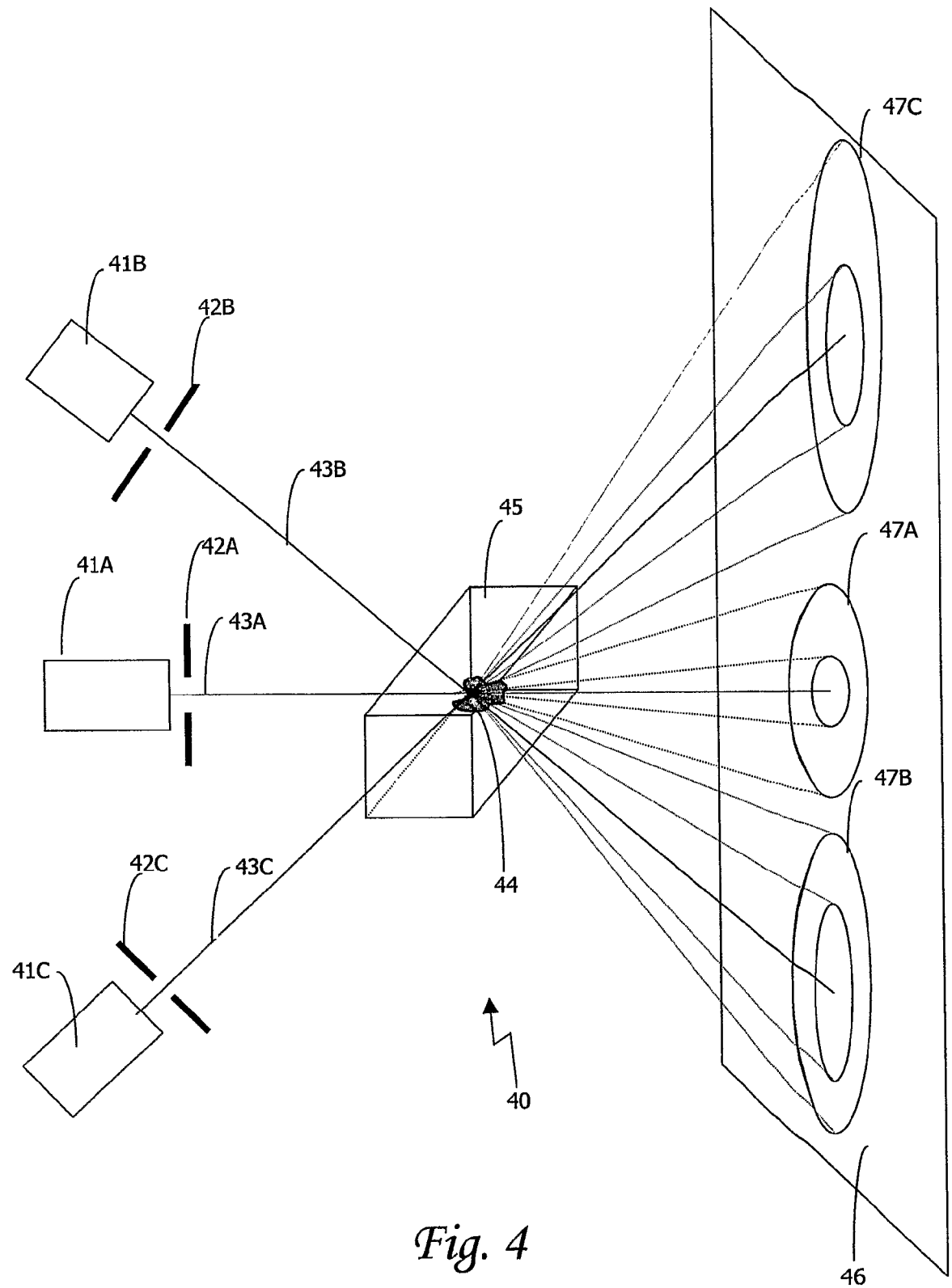
Figure 5:
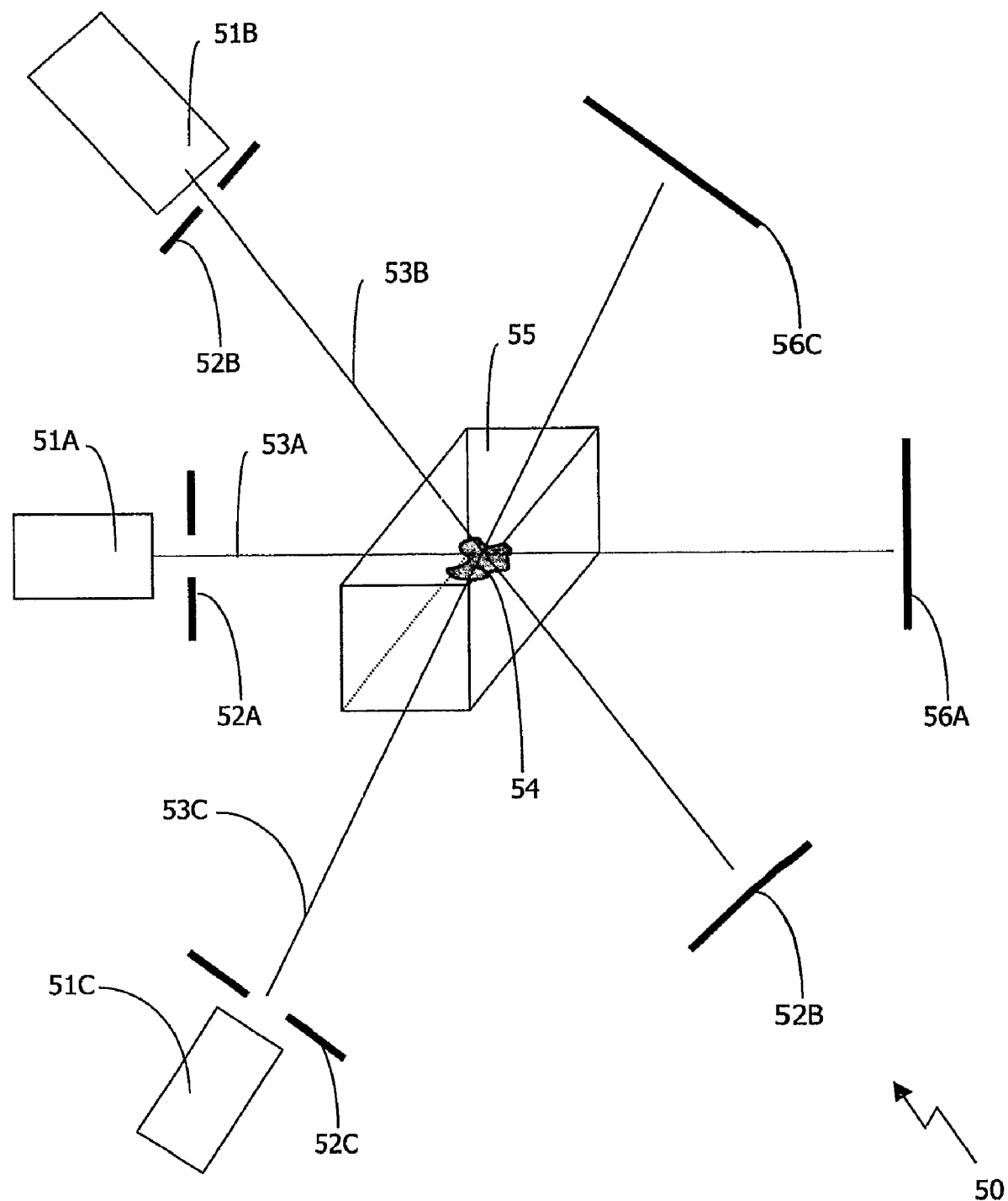
Figure 6:
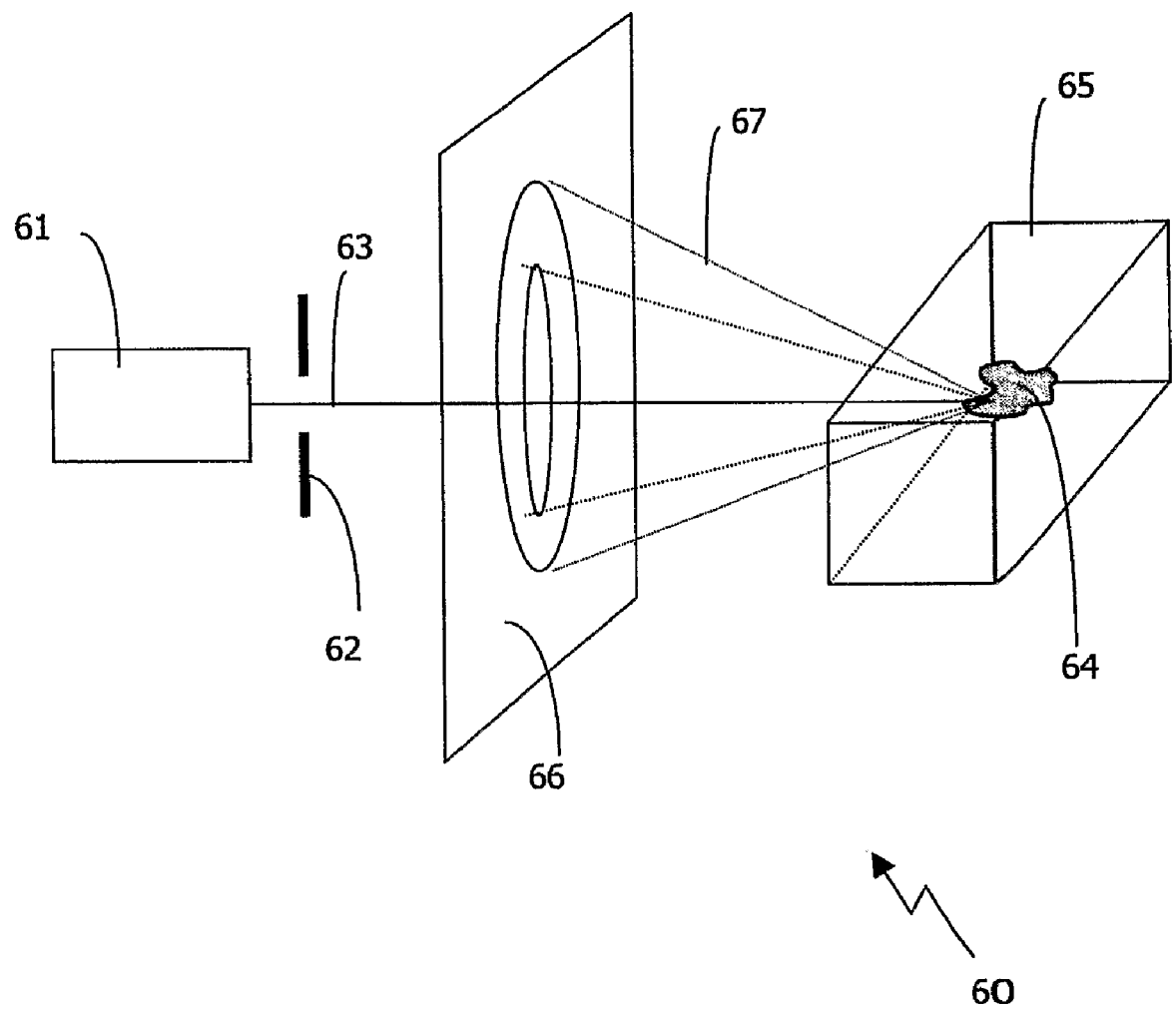
Figure 7:
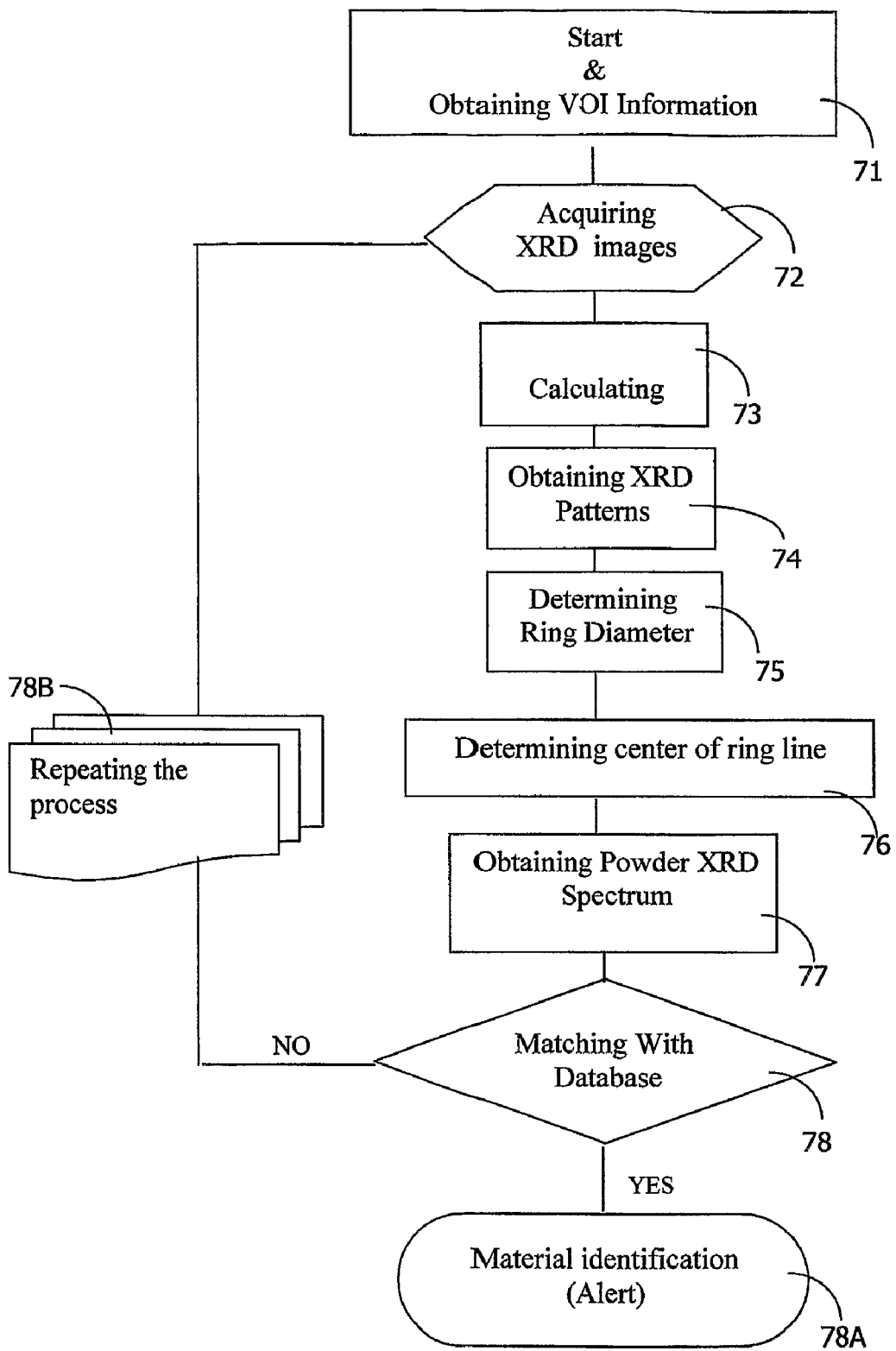
Figure 8:
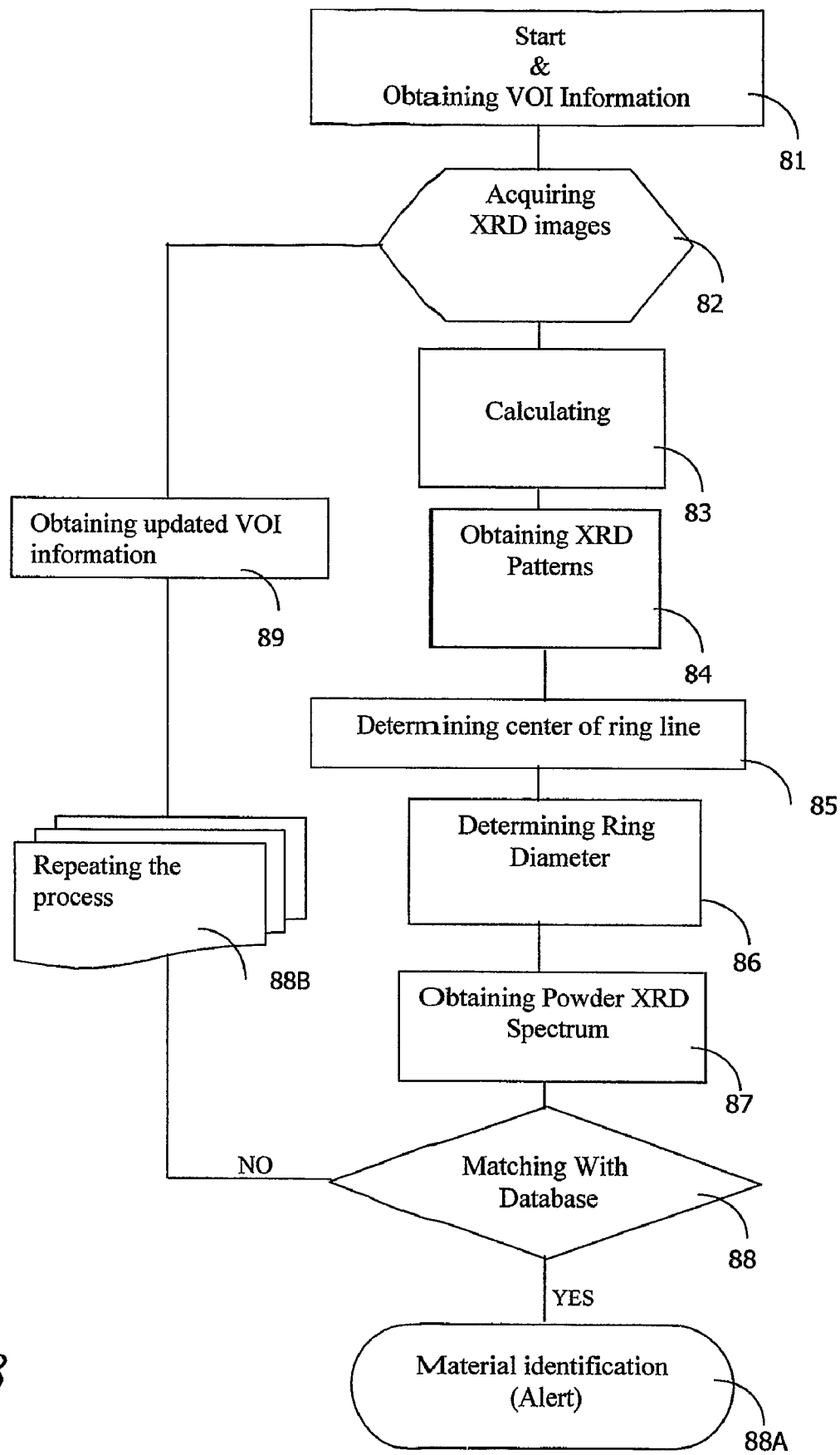
Figure 9:
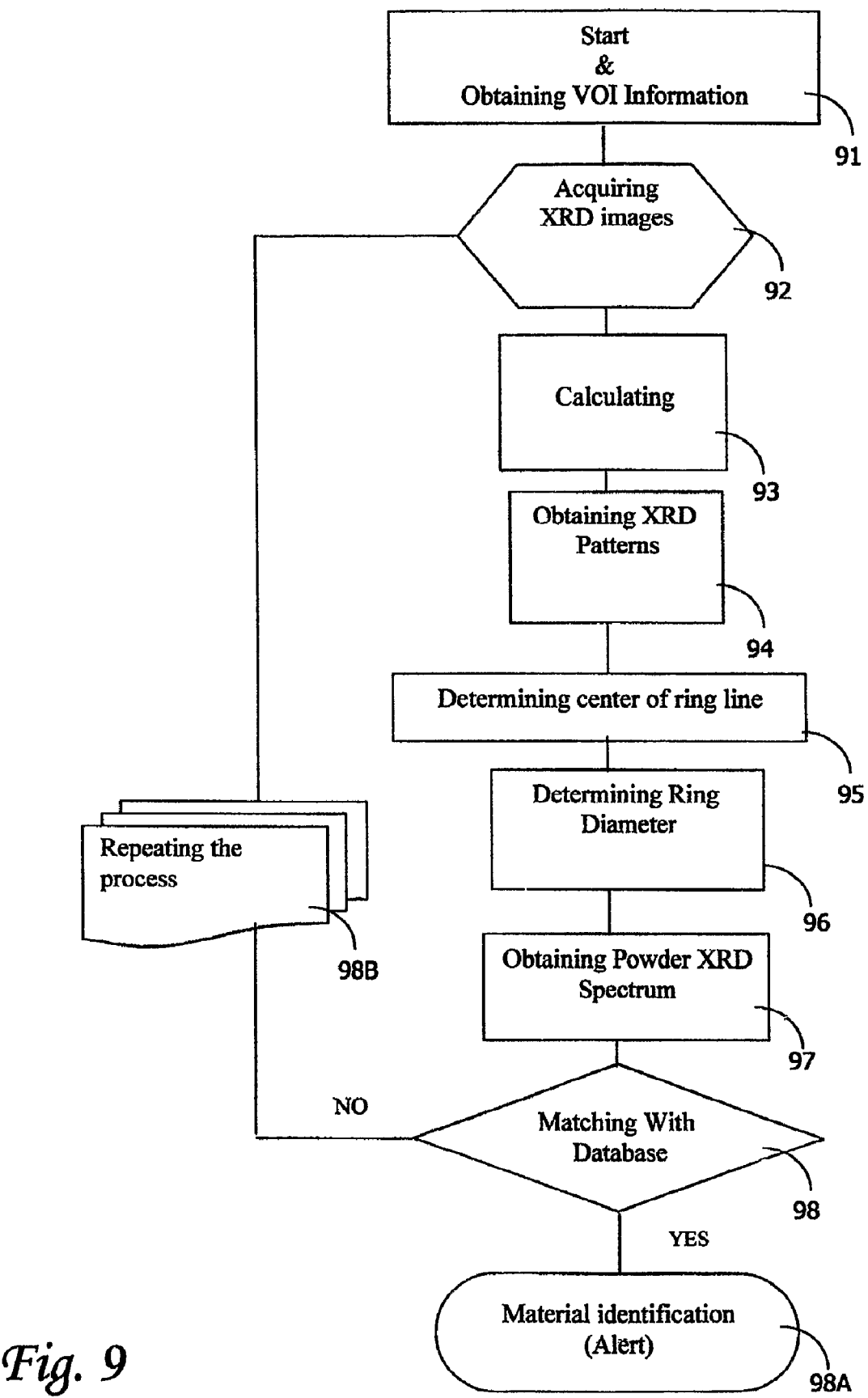
Figure 10:
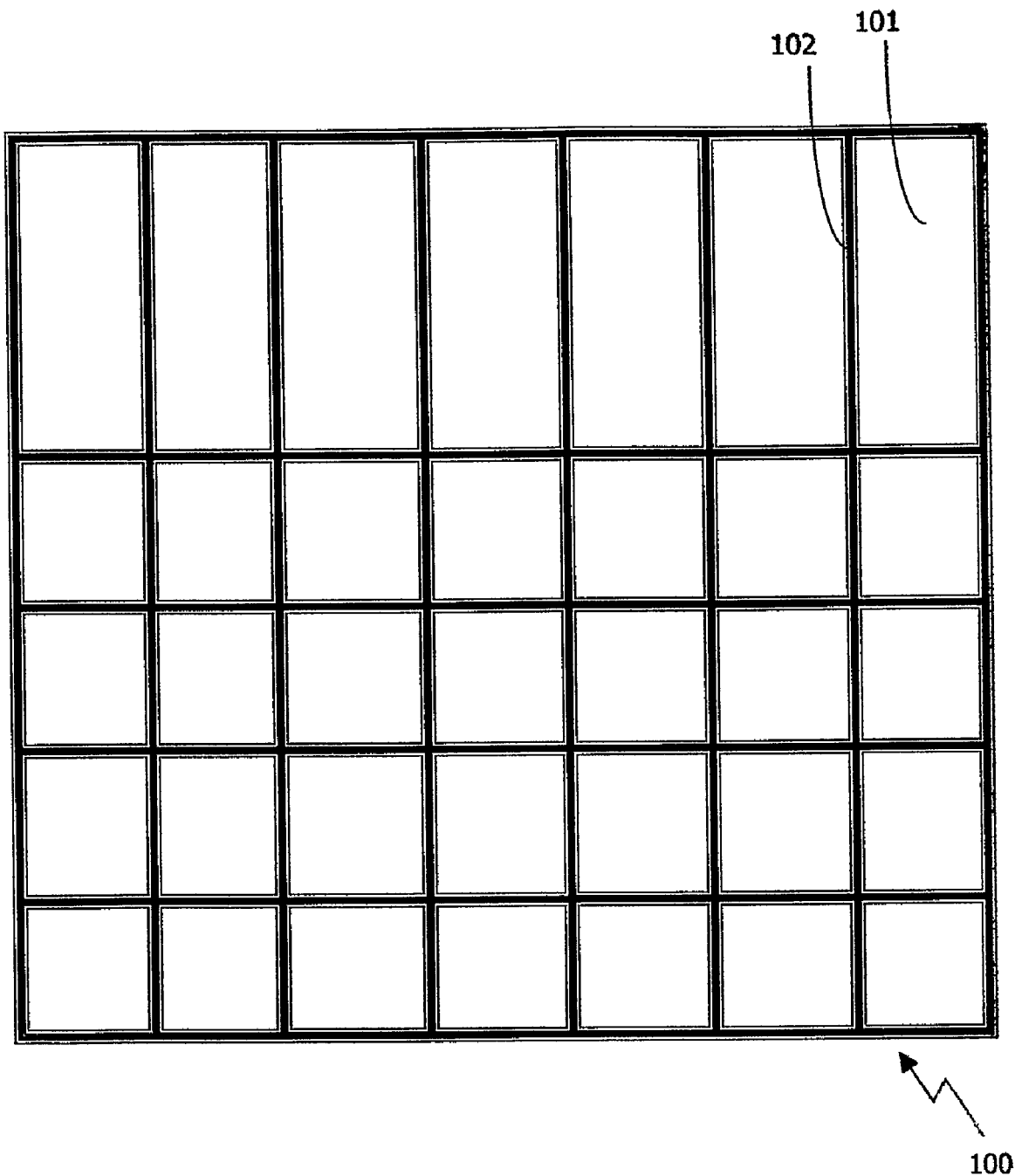

In order to understand the invention and to see how it may be implemented in practice, a plurality of embodiments will now be described, by way of non-limiting example only, with reference to the accompanying drawings, in which FIG. 1 schematically presents a typical powder X-ray diffraction ring pattern, also known as a "Debye-Scherrer" pattern, in a view comprising only the middle portion of the ring; a diffraction characterized by a set of three 4θs is presented (right hand view); a back-diffraction characterized by a set of three 360°-4θ is also presented (left hand view);

FIG. 2 schematically presents a remote XRD means for identifying the content of the volume of interest (VOI) according to one embodiment of the present invention;

FIG. 3 schematically presents a remote XRD means for identifying the content of the VOI according to yet another embodiment of the present invention;

FIG. 4 schematically presents a remote XRD means for identifying the content of the VOI according to yet another embodiment of the present invention;

FIG. 5 schematically presents a remote XRD means for identifying the content of the VOI according to yet another embodiment of the present invention;

FIG. 6 schematically presents a remote back-scattered XRD means for identifying the materials located in the VOI according to yet another embodiment of the present invention;

FIG. 7 schematically presents a method for identifying materials located in the VOI according to one embodiment of the present invention;

FIG. 8 schematically presents a method for identifying materials located in the VOI according to yet another embodiment of the present invention;

FIG. 9 schematically presents a method for identifying materials located in the VOI according to yet another embodiment of the present invention; and, FIG. 10 schematically presents a Cell-X detector according to yet another embodiment of the present invention.

SUMMARY OF THE INVENTION

It is thus one object of the present invention to provide a useful remote XRD means for identifying the materials located in a volume of interest (VOI). Said means comprise a plurality of N X-ray sources targeted towards said VOI adapted to emit a well characterized X-ray beam (i.e., shot) towards the target, wherein N is an integer greater than 1, preferably from 1 to 20; a plurality of M two dimensional (2D) X-ray detectors adapted to receive diffracted X-rays so an image comprising at least a portion of the obtained XRD patterns is obtained; where M is an integer greater than 1, preferably from 1 to 100; a processor adapted to measure said patterns; a database comprising records of patterns' parameters characterizing predetermined material; said database comprising records of materials that a notification should be provided when identified; and an alerting means adapted to alert the operator when the identified material in the VOI is one of said predetermined groups. This means is potentially adapted to identify sampled moving VOIs in a non-intrusive manner. It may further comprise suitable means to sample the material in the VOI so that the operator is notified of the presence of the material; and means to track or follow up said VOI before identifying its nature. Those remote XRD means are preferably adapted to alert either online or offline, to alert to a predetermined remote location, to be in communication with effective means adapted to isolate or immobilize said VOI transport until subsequent notification or any combination thereof.

It is acknowledged in this respect that one X-ray source may be providing for a plurality of shots. Hence a single 2D X-ray detector may be synchronized to detect each shot in a way that it is centered and relocated at a perpendicular position to the beam or a plurality of 2D X-ray detectors, which are synchronized, with the beam of the shot.

It is another object of the present invention to provide a method for acquiring an XRD image of a material inside a VOI. This method comprises the steps of receiving VOI coordinates from a lower stage system; irradiating the material in the VOI; acquiring Debye-Scherrer XRD patterns of the material in the VOI; extracting Debye-Scherrer XRD patterns; converting said XRD patterns (e.g. rings) of said VOI to standard powder X-ray diffraction spectra; searching and/or matching records in a database for material identification; and then, alerting in case said material matches a predetermined record. It is well in the scope of the present invention wherein this method is provided by the means as defined in any of the above; wherein backscattering is obtained and/or wherein energy information is collected in addition to the imaging calculations via the use of a Cell-X detector or Gamma Camera.

DETAILED DESCRIPTION OF THE INVENTION

The following description is provided, alongside all chapters of the present invention, so as to enable any person skilled in the art to make use of said invention and sets forth the best modes contemplated by the inventor of carrying out this invention. Various modifications, however, will remain apparent to those skilled in the art, since the generic principles of the present invention have been defined specifically to provide a remote process for identifying hazardous materials such as explosives in a VOI by means of an XRD based system.

It is the object of the present invention to provide a cost effective, secure, reliable and rapid system for enabling remote detection of hazardous materials and thus to provide for passengers and/or their carry-on luggage to walk in a reasonably wide corridor while being examined by the system.

The term 'materials in a volume of interest' is related to hazardous materials, such as explosives, flammable or toxic materials, chemical and biological warfare substances in either gas, liquid or solid states, drugs and narcotics, radioactive agents etc., and to metallic materials, such as iron, gold, platinum and any other valuable crystalline materials (e.g. ceramics), which are suitable for XRD analysis. The VOI is hence denoted according to the present invention as any 3D volume to be analyzed.

According to one embodiment of the present invention, those materials are related to any of the hereto-defined hazardous or crystalline materials, being carried by a passenger and/or in his carry-on luggage, especially in airports and similar locations. According to one specific embodiment of the present invention, said material is selected from any explosive materials. According to yet another specific embodiment of the present invention, said material is selected from any chemical or biological warfare agents.

It is in the scope of the present invention wherein the material in the VOI is located, analyzed, identified, and marked by any means, such as X-ray Imaging system, average density identification by Multiple Energy X-ray system, NMR (MRI), NQR, Laser Spectroscopy, IR imaging, millimeter wave imaging, THz imaging, etc.) as a first step, and then said material is further analyzed by the remote XRD means as defined and described in the present invention. The surveillance of and follow-up after the VOI identified at the first step may be provided by various video techniques or other means adapted for online image processing, whereat said VOI is transferred along a predetermined course, on a conveyor belt etc. and especially whereat said VOI is transferred along a non-predetermined course (e.g., incidental movement of a passenger with his carry-on luggage in a corridor).

It is in the scope of the present invention wherein said material in the VOI is a subject of imaging by a system comprising a combination of a plurality of X-ray sources and a plurality of X-ray detectors. Additionally or alternatively, said VOI is a subject of a sequence of subsequent imaging steps ('shots') taken by the aforementioned complex system, so that reliable and rapid analyses are provided.

The term 'XRD' refers to any method for determining the nature of a sample by calculating its diffraction pattern in either scattered or back-scattered techniques. Moreover, the term XRD also refers to any scattering or back-scattering system and/or to an incorporated system comprising XRD or back-scattered XRD with analyzing means adapted for energy or energetic detection, such as a Detector Array system which provides energy characteristics of the X-rays scattered by the material in the VOI, or a combination of detectors which provides simultaneous energy and image characteristics of the X-rays scattered by the material in the VOI.

The system basically consists of a collimated X-ray source synchronized with a 2D detector array. The X-ray source provides a narrow collimated beam that passes through the VOI. The X-rays are diffracted from the sampled material (and its neighboring materials which are in the X-ray beam path). The diffracted pattern is recorded by the two-dimensional array. Image processing is applied in order to define the number, diameter, intensity and broadening of the XRD patterns (e.g. the Debye-Scherrer rings). The XRD patterns are converted to standard powder XRD patterns and existing or proprietary search/match utilities or software (such as commercially available Rietveld based software) can be used to identify the material.

Reference is now made to FIG. 1, schematically presenting a plurality of Debye-Scherrer rings in a narrowed view, which comprises the central portion of the ring. This diffraction is characterized by an exit hole (1) and a set of three 4θs (See (2) for example). Adjacent to the left side of the presentation, a back-diffraction is provided, wherein the insert hole (3) is surrounded by a set of three 360°-4θs (See (4) for example).

Reference is now made to FIG. 2, schematically presenting one embodiment of the present invention wherein a plurality of XRD patterns (1-3) located at various spatial positions are acquired by one X-ray source and one mechanically synchronized 2D detector. Here, one X-ray source (e.g., an X-ray generator) is synchronized with a detecting plate in a way that the beam passes through the VOI. The X-ray generator is being moved between pluralities of predetermined locations, and the location of the detecting plate is synchronized with it. The process is repeated in order to improve the detection rate. The x-ray source (21) produces a sufficient amount of X-rays, which are potentially processed by a means of a collimator (22) before said processed X-rays (23) reach the VOI (24) accommodated in a container (25). According to the present invention, such an X-ray producing means (20) comprises an X-ray source (21), a collimator (22) or any other means adapted to process the X-rays produced in order to provide an effective X-ray beam (e.g. a focusing element). The diffracted X-rays are obtained by a means of at least one 2-dimensional detector (26) so that a measurable plurality of XRD patterns (27) is obtained. Locations (1-3) are the positions of the x-ray source wherein (1', 2', 3') are the relative positions of the aforementioned 2D detector (26).

Reference is now made to FIG. 3, schematically presenting a moving VOI, e.g., an object being transferred or a passenger walking with his carry-on-luggage, whereat a plurality of X-ray beams are emitted in the manner the beams are synchronized with the X-ray detectors. FIG. 3 is thus schematically presenting a novel non-intruding system (30) according to yet another embodiment of the present invention, which is especially adapted for obtaining multiple X-ray diffractions. This system (30) is especially useful for analyzing moving VOIs, and comprises an X-ray source, such as source (31), which is adapted to emit X-rays over a VOI (33) being moved along a corridor (32) in the direction (D). The X-ray source (31) is emitting a beam (A) over the sample located in site 34, so the diffraction is recorded by the 2D detector 37A; and a plurality of other beams directed to another one or more predetermined angles and directions, synchronized with the new location of the VOI at each particular time. For example, source (31) directs its beams in a manner such that the VOI is sampled along its travel (D) on conveyor (32), namely at locations 35 and 36, by beams B and C, so that diffractions B' and C' are provided on 2D detectors 37B and 37C, respectively.

Reference is now made to FIG. 4, schematically presenting another embodiment of the present invention, wherein the system is adapted to obtain a plurality of XRD pattern images on one 2D detector from a plurality of x-ray beams. FIG. 4 hence illustrates a system wherein a plurality of shots are taken either by a plurality of X-ray generators or one moving X-ray generator; wherein all the XRD patterns are detected on one big detecting plate. Each shot is taken in a manner such that the beam passes through the VOI. Here for example, three X-ray sources are provided, 41A-C. Each source comprises an X-ray source and a collimator or any equivalent device (42A-C). Hence, three X-ray beams (43A-C) are directed towards the VOI (44) located in a container (45). Each beam targets a predetermined position at the 2D detector (46), such that three XRD patterns (47A-C, respectively) are obtained.

Reference is now made to FIG. 5, schematically presenting another embodiment of the present invention, adapted to obtain multiple XRD patterns simultaneously using a plurality of X-ray beams and a plurality of 2D detectors. Here, a plurality of X-ray sources (e.g., X-ray generators) are targeted towards an identical number of X-ray detectors (e.g., detecting plates) while each of them is synchronized to penetrate the VOI. It is acknowledged in this respect that any number of X-ray sources and detectors are applicable in a variety of combinations, and different source to detector ratios are possible. Here, three X-ray sources (51A-C) are presented. Each source comprises an X-ray source and a collimator or any equivalent device (52A-C). Hence, three X-ray beams (53A-C) are directed towards the VOI (54) accommodated in a container (55). Each XRD provided by said three beams targets a predetermined 2D detector (56A-C).

Reference is now made to FIG. 6, schematically presenting yet another embodiment of the present invention, a system (60) that is adapted to obtain at least one back-scattered XRD. The X-ray source (61) generates at least one beam (63) targeted towards the sample in the VOI (64) in a container (65) such that a back-scattered beam (63) is recorded on a 2D detector (66). It is further acknowledged that system (60) may be used simultaneously with one or more other back-scattering systems and/or with one or more systems as defined and described above, such as aforementioned systems 20, 30, 50 etc.

It is the object of the present invention to provide a useful and remote method for identifying the content of a VOI. It is thus according to yet another embodiment of the present invention wherein the aforementioned process comprises the following general steps:

i. receiving VOI coordinates from lower stage system;
ii. irradiating the material in said VOI by one or a plurality of collimated X-ray beam(s);
iii. acquiring XRD pattern results from each impinging X-ray beam;
iv. extracting the XRD pattern of the material;
v. converting the ring XRD pattern of the material to a standard powder X-ray diffraction spectrum (Intensity against 2θ);
vi. searching and/or matching a database for material identification (e.g. according to the Rietveld method); and then,
vii. alerting (Y/N).

Reference is now made to FIG. 7 presenting a schematic flow chart of another embodiment of the present invention; wherein in step (71) information concerning the VOI, i.e., X, Y & Z information, is obtained by a prior step of allocating the VOI (not shown here). The collimated X-ray beam is targeted towards the center of the VOI.

A set of images of an XRD pattern or patterns (i.e., rings) of the VOI obtained by 2D detector array is acquired at step (72). Now at step (73), a plurality of calculations on each image is provided to complete missing or unclear arcs in the ring shape. Step (74) comprises the application of subtraction calculations or any other image processing calculations adapted to find the common XRD pattern of said VOI as it appears in the set of all images. At the following step (75), the center of broadening of the ring line is determined, especially for thick or (diffuse) blurred lines. In some cases, the entire ring pattern may not revealed, but rather a part of it. It is possible to find the required data from a part of the ring only. Also, calculations on the average perimeter of the ring will allow higher reliability. Subsequently at step (76), the ring diameter is determined, in the manner that ring intensity and ring broadening of the extracted VOI pattern is obtained. At step (77) the ring pattern is converted to powder XRD spectrum. Then, at step (78), matching the obtained XRD pattern with known materials in database is provided, wherein at case of matching, the VOI is positively identified. It is acknowledged in this respect that when hazardous materials are identified, an effective inline or offline alert is provided (78A). If such matching is not provided (78B), a general alert or a specific notification is provided, and the aforementioned process is repeated in the manner that a plurality of XRD images and/or other analytical characterizations are subsequently taken from different angles. In the case that after N states, wherein N is an integer greater than 1, the system has not absolutely identified the material as hazardous, but the possibility of the existence of such material does exist, then a special alert will be given to the operator.

It is acknowledged in this respect that the term 'alarm' according to the present invention refers to any notification given to either a remote site or to the operator located adjacent to the system. The alert is selected in a non-limiting manner from alarm, applicable especially when hazardous materials are detected in the VOI; all-clear notification, especially applicable when non-hazardous materials are present in the detected VOI and/or wherein the VOI is analyzed to be non hazardous; and notification per se; applicable especially wherein the system is operated in a specific mode of recording the nature/composition of goods and/or materials passing throughout a predetermined path.

Reference is now made to FIG. 8 presenting a schematic flow chart of another embodiment of the present invention; wherein in step (81) VOI information, i.e., X, Y & Z information is obtained by a prior step of allocating the VOI (not shown here). During the examination, a sub-system tracks the VOI, and supplies its (changed) coordinates when required. The collimated X-ray beam is targeted towards the center of the VOI. A set of images of an XRD pattern or patterns (e.g., rings) of the VOI obtained by 2D detector array is acquired at step (82). Now at step (83), a plurality of calculations on each image is provided to complete missing or unclear arcs in the ring shape. Step (84) comprises the application of subtraction calculation, adapted to find the common XRD pattern of said VOI as it appears in the set of all images. At the following step (85), the center of the ring line is determined, especially for thick or diffuse lines. Subsequently at step (86), the ring diameter is determined, such that ring intensity and ring broadening of the extracted VOI pattern is obtained. At step (87) the ring pattern is being converted to a powder XRD spectrum. Then, at step (88), matching the obtained XRD pattern with known materials in the database is provided, wherein in the case of matching, the material in the VOI is positively identified (hazardous material is identified) and an alert is provided (88A). If such a matching is not provided, the aforementioned process is repeated (88B). In this manner, a plurality of XRD images or other analytical characterizations are subsequently taken from different angles regarding the moving target. The new VOI coordinates are supplied to the system from a tracking sub-system (89). In the case that after N states, wherein N is an integer greater than 1, the system has not absolutely identified the material as hazardous, but a possibility for the existence of such material does exist, then a special alert will be given to the operator.

Reference is now made to FIG. 9 presenting a schematic flow chart of yet another embodiment of the present invention; wherein in step (91) VOI information, i.e., X, Y & Z information is obtained by a prior step of allocating the VOI (not shown here). A plurality (e.g., three) of collimated X-ray beams is targeted towards the center of the VOI, where each X-ray generator is located at a different location. A set of images of a complex XRD pattern or patterns (e.g., rings) of the material in the VOI obtained by 2D detector array is acquired at step (92). Now at step (93), a plurality of calculations on each pattern is provided to complete missing or unclear arcs in the ring shape. Step (94) comprises the application of subtraction calculation, adapted to find the common XRD pattern of said VOI as it appears in the set of all images. At the following step (95), the center of the ring line is determined, especially for thick or diffuse lines. Subsequently at step (96), the ring diameter is determined, taking into account the ellipsoidal shape of some of the patterns, in the manner that ring intensity and ring broadening of the extracted material pattern is obtained. At step (97) the ring pattern is converted to a powder XRD spectrum. Then, at step (98), matching the obtained XRD pattern with known materials in database is provided, wherein in the case of matching, the material is positively identified (when a hazardous material is identified, an alert is provided) (98A). If such matching is not provided, an alert is provided, and the aforementioned process is repeated (98B) such that a plurality of images or any other analytical characterizations are subsequently taken using the plurality of sources regarding the moving target. In the case that after N states, wherein N is an integer greater than 1, the system has not absolutely identified the material as hazardous, but a possibility for the existence of such material does exist, than a special alert will be given to the operator.

Reference is now made to FIG. 10 presenting a novel multi-functional detector array adapted for a flexible cellular-XRD technology (100), according to yet another embodiment of the present invention, denoted hereinafter by the term 'Cell-X'. The technology is especially useful for remote detection of explosive materials, and is based on combining XRD imaging with acquisition of energy information. The detector comprises two general ingredients: imaging detectors (101), and an energy means (spectrometer detector) (102), similar to those known in the art. These commercially available means are adapted for the detection of the XRD patterns (e.g., Debye-Scherrer rings) on a 2D pixel array detector. According to a more specific embodiment of the present invention, which is described in FIG. 10, each "unit cell" consists of a 2D array detector surrounded by a plurality of stripes of one-dimensional or a very narrow (very thin) two-dimensional array of detector elements able to resolve photon energies (i.e., perform spectroscopic measurements), such as stripes of solid state single crystal detectors, stripes of scintillation detectors etc. The Cell-X comprises small, medium, or large unit cells or any combination thereof. According to one embodiment of the present invention, the size of the Cell-X is approximately that of a human-being (220 cm×80 cm), enabling XRD examinations of a passenger entering the gate area of an airport when walking with his carry on luggage. Cell-X provides imaging information, while simultaneously is providing energy information, so XRD patterns are recognized as part of the imaging while energy information can be collected from each spectroscopy detector element (pixel) crossed by an XRD pattern.

The "flexibility" of the Cell-X is in its cell sizes and ratio between the imaging arrays and the spectroscopy stripes (arrays). It may vary from very large imaging arrays surrounded by spectroscopy stripes, through small imaging arrays surrounded by spectroscopy arrays of varying thicknesses, up to a unit in which the actual spectroscopy array will be the whole array detector. This Cell-X array consisting entirely of a spectroscopy array may serve as a Gamma Camera, but for our remote detection needs it will work as follows: (i) the array has now a dual capability (imaging and spectroscopy) all over the array; (ii) the whole array will serve as an imaging array, and will work like any of the above mentioned imaging arrays; and (iii) the whole array will serve as a spectroscopy array. Certain pixels, which are part of the XRD patterns, will be analyzed for energy information, in order to speed up the recognition process. It should be noted that the number and the location of each pixel to be energetically analyzed may vary from a predetermined location for each sampled pixel and the number of pixels up to the case in which the number of pixels to be sampled and their locations coincide.

The invention claimed is:

1. A remote XRD means for identifying a material in a volume of interest (VOI) comprising:
   a. at least one X-ray source targeted towards said VOI;
   b. at least one X-ray detector adapted to receive diffracted X-rays so an image comprising at least a portion of the obtained XRD patterns is obtained;
   c. a processor adapted to measure said patterns;
   d. a database comprising records of patterns' parameters characterizing predetermined materials: said database comprising records of materials that a notification should be provided when identified; and,
   e. alerting means adapted to issue an alert when a material is identified that is one of the materials for which a notification should be provided when identified;

wherein the processor is adapted to measure at least a portion ($\leq 360°$) of the full Debye-Scherrer rings.

2. The remote XRD means according to claim 1, wherein the processor is adapted to measure the central portion of the XRD patterns.

3. A method for acquiring XRD images of a material in a VOI, comprising the steps of:
   a. receiving VOI coordinates from lower stage system;
   b. irradiating the material in the VOI;
   c. acquiring of Debye-Scherrer XRD patterns;
   d. extracting of Debye-Scherrer XRD patterns;
   e. converting said XRD patterns (e.g. rings) of said VOI to standard powder X-ray diffraction spectra;
   f. searching and/or matching records in a database for material identification; and then,
   g. alerting in case said material matches a predetermined record;

wherein said method enables identification of suspicious substances within said VOI with substantially high efficiency.

4. The method according to claim 3; wherein back-diffraction is provided.

5. The method according to claim 3; wherein the detector is a Cell-X, adapted for acquiring both VOI's XRD image and information about its energy profile.

* * * * *